United States Patent [19]

Hinckley et al.

[11] Patent Number: 5,120,503
[45] Date of Patent: * Jun. 9, 1992

[54] EXTRACTING DEVICE FOR EXTRACTING ANTIGENS

[75] Inventors: Charles C. Hinckley, Pittsford; Dennis R. Zander, Penfield; Thomas C. Littlefield, Rochester; Richard W. Bacchetta, Rochester; Scott H. Schwallie, Rochester, all of N.Y.

[73] Assignee: Eastman Kodak Company, Rochester, N.Y.

[*] Notice: The portion of the term of this patent subsequent to Nov. 6, 2007 has been disclaimed.

[21] Appl. No.: 381,219

[22] Filed: Jul. 14, 1989

[51] Int. Cl.⁵ .............................. B01L 3/00
[52] U.S. Cl. ............................ 422/102; 422/57; 422/58; 422/61; 435/294; 435/295; 356/246
[58] Field of Search ............. 422/57, 58, 59, 61, 422/68.1, 101, 102, 104; 435/294, 295; 206/219, 521; 356/246

[56] References Cited

U.S. PATENT DOCUMENTS

| | | | |
|---|---|---|---|
| 3,680,967 | 8/1972 | Engelhardt | 356/246 |
| 3,814,522 | 6/1974 | Clark et al. | 356/197 |
| 3,933,440 | 1/1976 | Woolley | 422/102 |
| 3,961,899 | 6/1976 | Trivedi et al. | 422/102 |
| 4,073,693 | 2/1978 | Janin | 422/102 |
| 4,162,003 | 7/1979 | Bartos et al. | 206/215 |
| 4,234,316 | 11/1980 | Hevey | 23/230 |
| 4,427,634 | 1/1984 | Truglio | 422/99 |
| 4,473,530 | 9/1984 | Villa-Real | 422/104 |
| 4,528,187 | 7/1985 | Truglio | 422/102 |
| 4,639,419 | 1/1987 | Olson et al. | 435/5 |
| 4,673,639 | 6/1987 | Slifkin | 435/36 |
| 4,720,374 | 1/1988 | Ramachandran | 422/102 |
| 4,746,614 | 5/1988 | Devaney, Jr. et al. | 435/295 |
| 4,770,853 | 9/1988 | Bernstein | 422/102 |
| 4,808,524 | 2/1989 | Snyder et al. | 435/36 |
| 4,968,486 | 11/1990 | Zander | 422/102 |

Primary Examiner—David L. Lacey
Assistant Examiner—Jeffrey R. Snay
Attorney, Agent, or Firm—Dana M. Schmidt

[57] ABSTRACT

There is described a container used to extract antigens for an immunoassay, having a wall means defining open and closed opposite ends. The container is provided with dividing members located in the closed end of the container which divides the volume of the closed end into at least two separate regions. A portion of the container's wall means adjacent to the closed end is shaped and sized to cooperate with a depositing device to ensure that separate reagents are separately deposited on opposite sides of the dividing members.

12 Claims, 3 Drawing Sheets

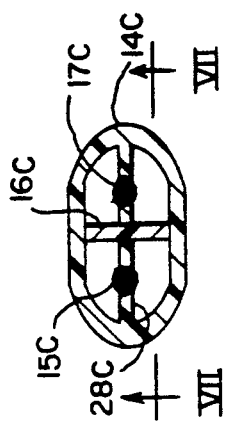
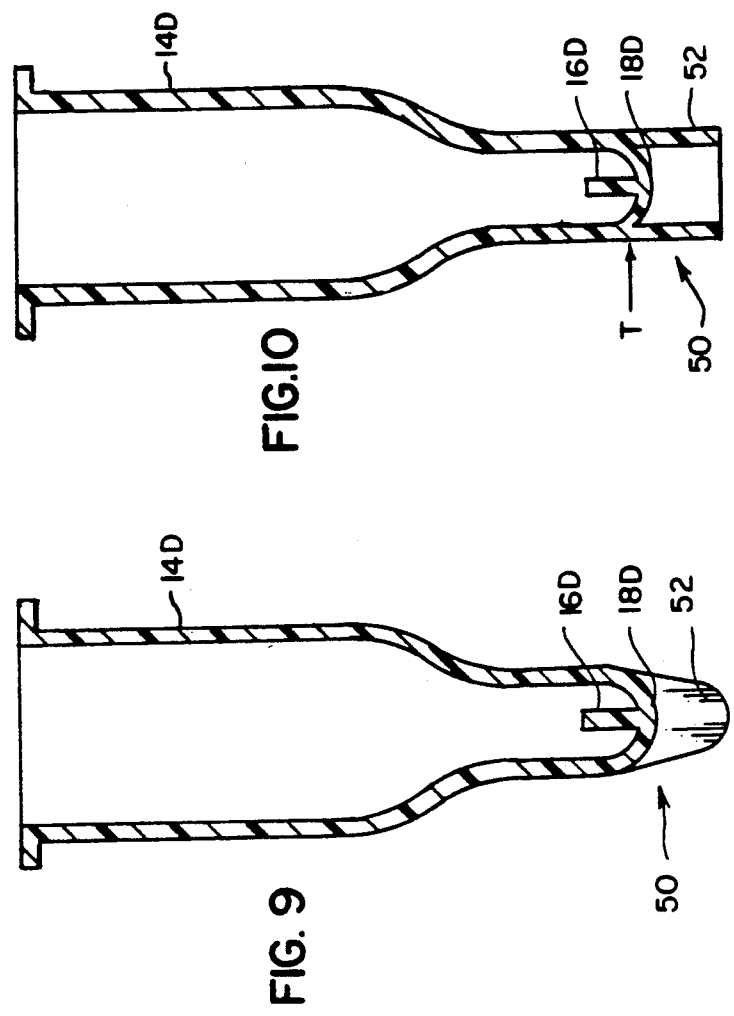
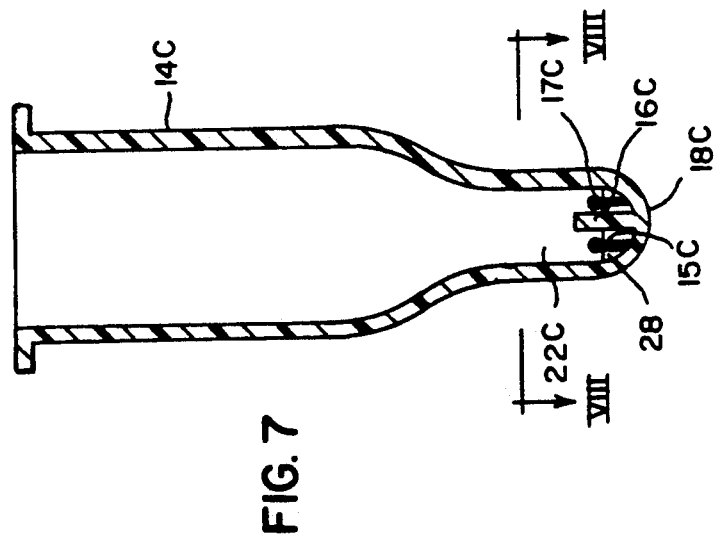

EXTRACTING DEVICE FOR EXTRACTING ANTIGENS

FIELD OF THE INVENTION

This invention relates to the construction of containers used to contain reagents for an assay, for example, to extract antigens for an immunoassay.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies, using an extraction procedure. For the test to be commerically successful, the extraction also needs to be relatively inexpensive, simple to use and rapid.

Examples of organisms which can be detected by immunoassay are: (1) Chlamydia trachomatis (herein C. trachomatis) which is one of two microbial species of the two microbial species of the genus Chlamydiaceae, order Chlamydiales. (2) Herpes simplex virus (HSV) which remains a serious problem. (3) Gonorrhea, which is a disease usually transmitted by sexual contact caused by a bacterium of the Neisseria genus, especially N. gonorrhea. (4) N. meningitidis and N. lactamica, which are also species of considerable medical and diagnostic interest.

In certain cases, it is necessary for reagents used in an extraction to be deposited in measured quantities and/or stored in an extraction container prior to its use resulting in more accurate and more rapid tests. An example of such an extraction container is more specifically discussed in U.S. Pat. No. 4,639,419 entitled "Immunological Color Change Test Involving Two Differently Colored Reagent Spots" issued on Jan. 27, 1987, disclosing a closed-ended tube where two reagents spots are placed into a well of the tube located in the closed end. Other patents disclosing deposits of reagents within an extraction device are U.S. Pat. Nos. 4,808,524 entitled "Test Kit and Method For The Determination of Streptococcus A Antigen" issued on Feb. 28, 1989, U.S. Pat. No. 4,673,639 entitled "Dry Form Microni- tray Acid Streptococci Extraction-Agglutination Test" issued on Jun. 16, 1987 and U.S. Pat. No. 4,746,614 entitled "Extraction Device" issued on May 24, 1988.

However, standard extraction containers have not been adequate in keeping extraction reagents separated during the depositing and drying process or storage while allowing for adequate mixing upon reconstitution and for proper orientation of the container. As a result, extraction reagents have been allowed to interact before drying causing neutralization and inaccurate test results. Also, standard extraction containers have not aided the retention of dried extraction reagents within the closed end.

Such inadequacies in extraction containers have greatly reduced the accuracy of existing immunoassays employing the use of extraction containers. Furthermore, the extraction container is limited as to structural features that can be included, since the side walls adjacent the closed end need to be flexible enough to allow the container to be squeezed, to aid in dissolving the extraction reagent.

Therefore, prior to this invention, there has been a need for an extraction container which assists in more rapid and more accurate detection of antigens in an immunoassay through the use of effective depositing, drying and storage of extraction reagents in the extraction container.

An additional need has been to have predetermined measured quantities of reagents deposited, dried and stored in the extraction container in a manner producing in a more precise analytical determination.

SUMMARY OF THE INVENTION

We have constructed an extraction container that is effective in solving the above-noted problems by separation of extraction reagents during drying and storage of reagents.

More specifically, in accordance with one aspect of the invention, there is provided a container useful for extracting antigens, comprising:

A. wall means defining open and closed opposite ends; and

B. dividing means located in the closed end of the container for dividing the volume of the closed end into at least two separate regions;

a portion of the wall means adjacent to the closed end being shaped and sized to cooperate with a depositing means to ensure deposit of reagents on either side of the dividing means.

In accord with another aspect of the invention, there is provided a container for storing reagents on a wall of the container. The container is improved in that the wall includes at least one raised rib over which a reagent is separately deposited, to anchor the reagent in place, the rib having a height less than that of the reagents.

In accord with still another aspect of the invention, there is provided a container used to extract antigens for an immunoassay comprising:

A. wall means defining open and closed opposite ends;

B. dividing means located in the closed end of the container for dividing the volume of the closed end into at least two separate regions; and C. orienting means on the container for orienting the dividing means with respect to a reagent-depositing means so that reagents are deposited by the depositing means on opposite sides of, and spaced from, the dividing means.

In accord with yet another aspect of the invention, there is provided a kit for extracting an antigen from body fluids, the kit including an extraction device in which two or more reagents are added, and a swab for insertion of body fluid specimen into the container and for mixing of the specimen and reagents, the improvement in which the extraction container used to extract the antigens for the immunoassay comprises:

A. wall means defining open and closed opposite ends;

B. dividing means located in the closed end of the container for dividing the volume of the closed end into at least two separate regions;

a portion of the wall means adjacent to the closed end shaped and sized to cooperate with a depositing means to ensure deposit of reagents on either side of the dividing means.

In accord with a further aspect of the invention, there is provided a method of depositing reagents in a closed end of a container comprising the steps of:

A. while placing a container in a holder, automatically forcing the container to have a fixed orientation by reason of means on the container for orienting the container relative to the holder, B. thereafter inserting a depositing means into the container, the depositing means having a predetermined orientation relative to the holder, and C. ejecting separate reagents from two different parts of the depositing means, whereby the separate reagents are separately deposited in a predictable location in the container.

Accordingly, it is an advantageous feature of the invention that the container is oriented automatically with respect to a depositing means to insure that separate reagents are deposited on opposite sides of a dividing means, thereby preventing premature interaction and neutralization.

Another advantageous feature is that such a container can be provided with means for aiding in the retention of deposited reagent.

Advantageous features other than those noted hereinabove will become apparent upon reference to the following Description of Preferred Embodiments when read in light of the attached drawings.

BRIEF DESCRIPTION OF THE DRAWINGS

FIG. 7 is a view similar to the elevational view of FIG. 1, but illustrating an alternate embodiment, taken along the line VII—VII of FIG. 8;

FIG. 8 is a section view of FIG. 7, taken along the line VIII—VIII of FIG. 7;

FIG. 9 is a section view similar to FIG. 7 but illustrating a separate embodiment;

FIG. 10 is a section view similar to FIG. 7 and 9, but illustrating a separate embodiment;

DESCRIPTION OF THE PREFERRED EMBODIMENTS

The invention is described hereinafter in connection with certain preferred embodiments wherein the extracted container is particularly suited for extracting antigens for immunoassays, requiring separation of deposited extraction reagents. It is also useful for deposited reagents used for other purposes.

Figure 2:
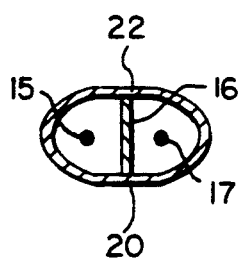
FIG. 2 is a section view taken generally along lines II—II of FIG. 1.
Figure 1:
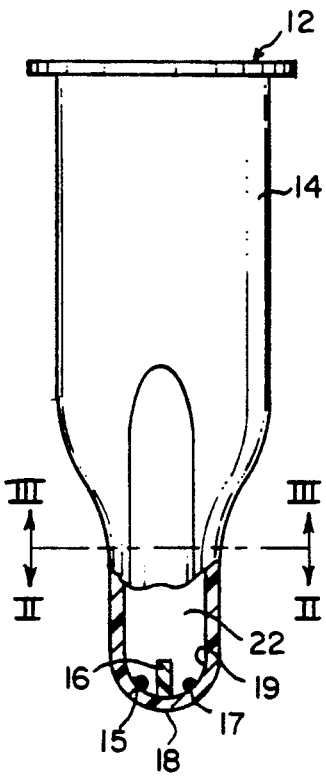
FIG. 1 is an elevational view, partly sectioned, of an extraction container constructed in accordance with the invention.
Figure 3:
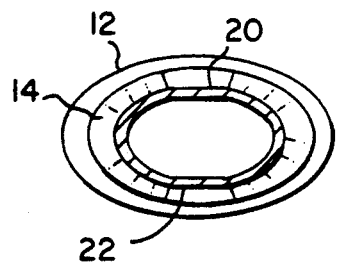
FIG. 3 is a section view of FIG. 1, taken generally along the line III—III.
Figure 4:
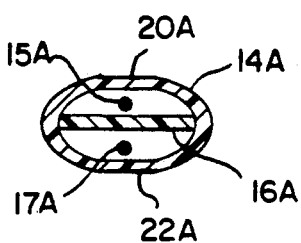
FIG. 4 is a view similar to FIG. 2 but illustrating an alternate embodiment.

The preferred extraction container, FIG. 1, has wall means 14 defining open and closed opposite ends 12 and 18, wherein a portion of wall means 14 is shaped so that it has at least one generally flat surface 22, and preferably also an opposite generally flat surface 20, FIG. 3, to automatically orient the container in a holder. Also included are dividing ridge 16 at closed end 18 of the container to ensure that separate reagents 15 and 17 are directed into at least two separate regions on the inside surface 19 of wall means 14. Flat surfaces 20 and 22 can have any predetermined angular orientation relative to dividing ridge 16. Two preferred orientations are as follows: one in which they extend generally perpendicular to the dividing ridge 16, FIG. 2, and one in which the flat surfaces 20A, 22A are generally parallel to the dividing ridge 16A as seen in FIG. 4. The flat surfaces 20, 22 or 20A, 22A primarily serve the purpose of orienting the container so that the dividing means 16 is in the correct position for a twin-channel depositing means. That is, when end 18 of the container is inserted into a holder (not shown), flat surfaces 20 and 22 or 20A, 22A automatically force the container to be properly oriented relative to the holder. The container will not insert into the holder until the flat surfaces 20, 22 are properly aligned with a flat surface in the holder. Because the twin-channel depositing means is already properly oriented relative to the holder, this in turn serves to orient the depositing means relative to the container, and specifically to the dividing ridge 16 or 16A. As a result, when the twin channels of the depositing means are activated, they deposit separate reagents on opposite, rather than the same, sides of dividing ridge 16 or 16A.

The preferred reagents used with this invention are dithiothreitol, a reducing agent, with polyacralamide, a stabilizer and TRISMA (tris-hydroxyaminomethane) which are used in the extraction of the chlamydial antigen.

Also useful, as described in U.S. Ser. No. 255,928, commonly owned and filed on Oct. 7, 1988 by Pronovost, et al and entitled "High pH Extraction Composition And Its Use To Determine A Chlamydial Gonococcal or Herpes Antigen", is a reagent composition for extracting antigen from chlamydial, gonococcal or herpes organisms having a pH of at least about 8 and comprising a strong base and an alcoholamine. Other addenda preferably included in the extraction composition include a cationic surfactant, one or more reducing agents, preservatives to prevent hydrogen peroxide activity and chelating agents. It is conceivable that either the strong base, the alcoholamine, the cationic surfactant or the reducing agent could be used for depositing and drying in this invention.

Examples of other reagents which could be deposited, dried, stored and used for other purposes in this invention are enzymes, enzyme substrates, antibodies, antigens, haptens, inorganic and organic reagents, buffers, salts and the like, as well as radioactively tagged or fluorescent reagents of the foregoing types including nonisotopic tags such as enzymes, cofactors, luminescent agents and the like.

Figure 5:
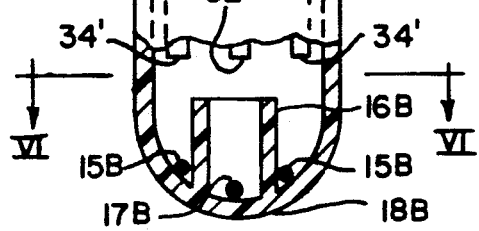
FIG. 5 is an elevational view similar to FIG. 1, but illustrating a separate embodiment and a depositing means for the reagents.
Figure 6:
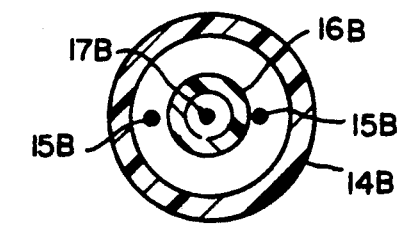
FIG. 6 is a section view of the embodiment illustrated in FIG. 5, taken along the line V—V.

An alternative embodiment of this invention is shown in FIG. 5 and FIG. 6. Parts similar to those previously described bear the same reference numeral to which the distinguishing suffix "B" is appended. Here, the dividing ridge, 16B, and wall means 14B, adjacent to the closed end 18B of the container are both shaped into an arc. The arc of dividing ridge 16B, is generally parallel to the arc of the wall means 14B, FIG. 6. Flats, as illustrated at 20, FIG. 1, would not be necessary in this embodiment for the purpose of orienting the container and the dividing means. The reason is as follows: a depositing means 30, FIG. 5, having turrets 32, 34 and 34' is constructed to deposit or eject reagent centrally, and on one or both sides. Since depositing means 30 has a snug fit within open end 12B, and ridge 16B is spaced to fit in between turrets 32 and 34, 34', the orientation is achieved automatically.

Dividing ridge 16, FIG. 1, and 16B, FIG. 5, are each sufficiently flexible for allowing it to be collapsed, in order to allow a swab to push against the dried reagents for proper mixing of the reagents during reconstitution. Some materials tested in the construction of the container cracked or showed signs of stress crack. The reagents used in the immunoassay in those cases would leak out of their region. It has been found that polyethylene or ethylene vinyl acetate are the preferred materials with which to construct the container. Preferably, dividing ridge 16 or 16A or 16B is no thicker than about 0.23 mm, to aid in flexibility.

The preferred embodiment, FIG. 1, has been found to be surprisingly effective in providing accurate, rapid results. Most importantly, it has been found to effectively store extraction reagents in a separated condition.

The embodiments as illustrated in FIG. 1 and FIG. 5 may also be constructed with a cross-rib, FIG. 7. The device of FIG. 7 is similar to the embodiment illustrated in FIG. 1. Parts similar to those previously described bear the same reference numeral to which the distinguishing suffix "C" is appended. Thus, the container has a closed end 18C, a dividing ridge 16C, and at least one flat surface 22C. However, in addition two raised ribs 28 are provided which have a height less than the height of each separate reagent deposit, FIG. 7. Preferably they extend generally perpendicular to dividing ridge 18C, FIG. 8. Extraction reagents are separately deposited over the raised ribs. The cross-ribs 28 serve the purpose of retention of deposits 15C, 17C, FIG. 8, of reagents in the closed end 18C of the container. The cross-ribs are preferred over cross-grooves or roughened surfaces as an anchoring means.

The container can also be constructed with a reinforcing means mounted on the closed end of the container for absorbing shock to prevent subsequent dislodging of dried reagents located in their separate regions, FIGS. 9 and 10. Parts similar to those previously described bear the same reference numeral to which the distinguishing suffix "D" is appended. Thus, the container has a dividing ridge 16D in closed end 18D. However, shock absorber means 50 are added, that extend from end 18D. Preferably the shock absorber comprises a flange 52 or a skirt 52' as shown in FIGS. 9 and 10, respectively. Other projections that would be apparent to one skilled in the art, can also be used. The shock absorber needs to attach at or below the tangent point of wall 14D, to keep that wall flexible for squeezing. As used herein, the "tangent point" is that point where the curved bottom end 18D attaches to a straight wall portion, e.g., point T, FIG. 10.

Preferably, the shock absorber means will resist the dislodging of a 0.016 g amount of dried reagent deposited in closed end 18D when the container, weighing 1.716 g in all, is dropped a distance of 76.2 cm onto a hard surface. A length of 0.254 cm and a thickness of about 1 mm for plastic flange 52 is a representative example of an embodiment that achieves such results.

Figure 11:
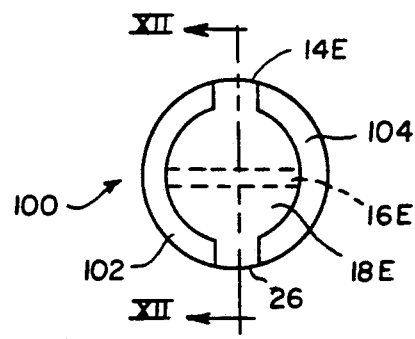
FIG. 11 is a bottom plan view of a device constructed in accordance with the invention, but illustrating an alternate embodiment.
Figure 12:
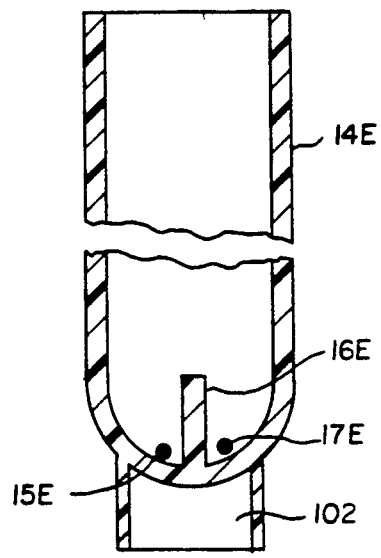
FIG. 12 is a fragmentary section view taken generally along the lines XII—XII of FIG. 11.
Figure 13:
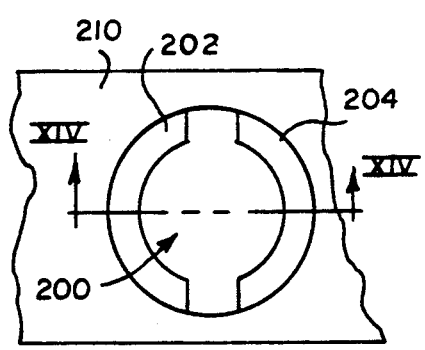
FIG. 13 is a plan view of the open end of a container holder constructed for engaging a container as illustrated in FIGS. 11 and 12.
Figure 14:
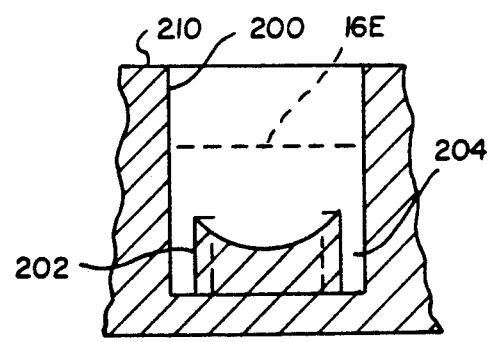
FIG. 14 is a fragmentary section view, taken along the line XIV—XIV of FIG. 13.

An alternate embodiment is illustrated in FIGS. 11-12 wherein a skirt for shock absorbance is also useful to orient the container. Parts similar to those previously described bear the same reference numeral to which the suffix "E" is appended. Thus, the container has wall means 14E defining open and closed opposite ends and dividing ridge 16E located in the closed end 18E of the container which divides the volume of the closed end 18E into at least two separate regions. In this embodiment, the container has orienting means 100 orienting dividing ridge 16E with respect to a reagent-depositing means. Preferably the orienting means 100 comprise two skirts 102 and 104 shaped and sized in two separate arcs generally opposite to each other on opposite sides of end 18E. The skirts are an extension of wall means 14E, and do not meet in a circle. These skirts cooperate with mating slots 202 and 204, in a hole 200 formed in a container holder 210, FIGS. 13 and 14. That is, skirts 102 and 104, FIG. 11, are shaped and sized to fit into the recessed mating slots 202 and 204, FIG. 13, of the container holder.

The extraction container of this embodiment is thus forced into proper orientation with holder 210, which is already oriented with a depositing means which is to be inserted into the open end of the container. The result is to force dividing ridge 16E to locate as shown in phantom, FIG. 14, so the depositing means can deposit reagent on opposite sides thereof.

The shock absorbing means is described and claimed per se in commonly-owed application U.S. Ser. No. 380,843 co-filed herewith by Dennis Zander, entitled "Device for Absorbing Shock to a Container", now U.S. Pat. No. 4,968,486.

Most preferably, the extraction container of this invention is packaged in a kit form. Although the extraction containers disclosed herein may be prepared at the time of their use, it is contemplated that they will find their greatest utility as pre-prepared and pre-packaged test kits to be used in clinics, hospitals, physicians' offices or in the home. Such a kit comprises the extraction container of this invention, a swab for insertion of body fluid specimen into the container and for mixing of the specimen and extraction reagents. Conveniently, all of this is packaged into a package.

The invention has been described in detail with particular reference to preferred embodiments thereof, but it will be understood that variations and modifications can be effected within the spirit and scope of the invention.

What is claimed is:

1. A container useful for extracting antigens, comprising:
   A. wall means defining open and closed opposite ends, a portion of said wall means defining said closed end being flexible enough to permit squeezing;
   B. dividing means located in the closed end of the container for dividing the volume of said closed end into at least two separate regions;
   a portion of said wall means adjacent to said closed end being shaped and sized to cooperate with a depositing means to ensure separated deposit of reagents on opposite sides of said dividing means, and further comprising
   C. means mounted on the closed end of the container extending from said closed end, for protecting the container from shock and subsequent dislodging of dried reagents located in said separate regions of said closed end of the container.

2. A container as defined in claim 1 wherein said wall means portion is shaped so that it has at least one flat surface to orient said container and said dividing means at said closed end to ensure that separate reagents are directed into said separate regions.

3. A container as defined in claim 2, wherein said flat surface extends generally parallel to said dividing means.

4. A container as defined in claim 2 wherein said flat surface extends generally perpendicular to said dividing means.

5. A container as defined in claim 1 wherein said portion of said container wall means adjacent said closed end and said dividing means is shaped in an arc, and said dividing means is generally parallel to the arc of said wall means.

6. A container as defined in claim 1 and further comprising means for anchoring deposits of reagents within said closed end of said container, and a deposit of reagents on said anchoring means.

7. A container as defined in claim 6 wherein said anchoring means comprise a raised rib over which said reagents are separately deposited, to anchor said reagents in place, said rib having a height less than the height of the separate deposits.

8. A container useful to extract antigens for an immunoassay comprising:
A. wall means defining open and closed opposite ends, a portion of said wall means defining said closed end being flexible enough to permit squeezing;
B. dividing means located in the closed end of the container for dividing the volume of said closed end into at least two separate regions;
C. orienting means on the container for orienting said dividing means with respect to a reagent-depositing means so that separate reagents are deposited by said depositing means on opposite sides of, and spaced from, said dividing means, and further comprising
D. means mounted on the closed end of the container extending from said closed end, for protecting the container from shock and subsequent dislodging of dried reagents located in said separate regions of said closed end of the container.

9. A container as defined in claim 8, wherein said orienting means comprise a flexible flange extending from said means mounted on said closed end, away from said dividing means.

10. A container as defined in claim 8 wherein said orienting means comprise at least one flat surface on said wall means to orient said container and said dividing means in a container holder.

11. In a kit for extracting an antigen from body fluids, the kit including an extraction device in which two or more reagents are added, and a swab for insertion of body fluid specimen into a container and for mixing of the specimen and reagents, the improvement
A. wall means defining open and closed opposite ends, a portion of said wall means defining said closed end being flexible enough to permit squeezing;
B. dividing means located in the closed end of the container for dividing the volume of said closed end into at least two separate region;
a portion of said wall means adjacent to said closed end being shaped and sized to cooperate with a depositing means to ensure deposit of reagents on either side of said dividing means, and further comprising
C. means mounted on the closed end of the container extending from said closed end, for protecting the container from shock and subsequent dislodging of dried reagents located in said separate regions of said closed end of the container.

12. In a container for storing reagents, the container including a wall on which said reagents are deposited, the improvement comprising said wall icluding a portion that is sufficiently flexible to permit squeezing of said portion, and at least one raised rib over which a reagent is deposited, to anchor the reagent in place, said rib having a height less than the height of the deposit anchored thereto,
and further comprising means mounted on the closed end of the container extending from said closed end, for protecting the container from shock and subsequent dislodging of dried reagents located in said separate region of said closed end of the container.

* * * * *